(12) United States Patent
Heuscher et al.

(10) Patent No.: US 7,180,975 B2
(45) Date of Patent: Feb. 20, 2007

(54) SYSTEM AND METHOD FOR EXACT IMAGE RECONSTRUCTION FOR HELICAL CONE BEAM COMPUTED TOMOGRAPHY INCLUDING REDUNDANT DATA

(75) Inventors: Dominic J. Heuscher, Aurora, OH (US); Kevin M. Brown, Mentor-on-the-Lake, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 64 days.

(21) Appl. No.: 10/545,201

(22) PCT Filed: Feb. 9, 2004

(86) PCT No.: PCT/IB2004/000365

§ 371 (c)(1),
(2), (4) Date: Aug. 10, 2005

(87) PCT Pub. No.: WO2004/072904

PCT Pub. Date: Aug. 26, 2004

(65) Prior Publication Data

US 2006/0133562 A1    Jun. 22, 2006

Related U.S. Application Data

(60) Provisional application No. 60/483,165, filed on Jun. 27, 2003, provisional application No. 60/447,428, filed on Feb. 14, 2003.

(51) Int. Cl.
*G01N 23/00* (2006.01)
(52) U.S. Cl. .............................. 378/4; 378/15
(58) Field of Classification Search .............. 378/4–20, 378/901
See application file for complete search history.

(56) References Cited

U.S. PATENT DOCUMENTS 4,293,912 A    10/1981   Walters ....................... 378/14

(Continued)

FOREIGN PATENT DOCUMENTS

EP    997 849 A2    5/2000

OTHER PUBLICATIONS

Katsevich, A., et al.; Evaluation and empirical analysis of an exact FBP algorithm for spiral cone-beam CT; 2003; Proc. of SPIE; 5032:663-674.

(Continued)

*Primary Examiner*—Courtney Thomas
*Assistant Examiner*—Alexander Taningco
(74) *Attorney, Agent, or Firm*—Thomas M. Lundin

(57) ABSTRACT

A conebeam computed tomography scanner (10) acquires conebeam projection data along a generally helical source trajectory around an examination region (14). An exact reconstruction processor (40) includes a convolution processor (42) and an aperture weighted backprojection processor (46, 66). The convolution processor (42) performs at least one convolution of the acquired projection data. The convolving operates on projection data falling within an exact reconstruction window (38) and on at least some redundant projection data falling outside the exact reconstruction window (38) to produce convolved projection data. The aperture-weighted backprojection processor (46, 66) performs aperture-weighted backprojecting of the convolved projection data using an aperture weighting function that weightedly combines at least some convolved redundant projection data with convolved projection data falling within the exact reconstruction window (38) to generate a reconstructed image with contributions from redundant projection data.

24 Claims, 9 Drawing Sheets

U.S. PATENT DOCUMENTS

| | | | | |
|---|---|---|---|---|
| 4,580,219 | A | 4/1986 | Pelc et al. | 382/131 |
| 5,170,439 | A * | 12/1992 | Zeng et al. | 382/131 |
| 5,406,479 | A | 4/1995 | Harman | 378/7 |
| 5,446,799 | A | 8/1995 | Tuy | 382/132 |
| 5,625,660 | A | 4/1997 | Tuy | 378/15 |
| 6,097,784 | A | 8/2000 | Tuy | 378/4 |
| 6,104,775 | A | 8/2000 | Tuy | 378/4 |
| 6,504,892 | B1 | 1/2003 | Ning | 378/4 |
| 2002/0015468 | A1 | 2/2002 | Kohler et al. | 378/4 |
| 2003/0174803 | A1 * | 9/2003 | Katsevich | 378/4 |
| 2004/0028173 | A1 * | 2/2004 | van de Haar | 378/4 |

OTHER PUBLICATIONS

Katsevich, A.; Microlocal Analysis of an FBP Algorithm for Truncated Spiral Cone Beam Data; 2002; J. of Fourier Analy; 8:407-425.

Katsevich, A.; Analysis of an exact inversion algorithm for spiral cone-beam CT; 2002; Phys. Med. Biol.; 47:2583-2597.

Noo, F., et al.; Exact helical reconstruction using native cone-beam geometries; 2003; Phys. Med. Biol.; 48:3787-3818.

Heuscher, D., et al.; Redundant data and exact helical cone-beam reconstruction; 2004; Phys. Med. Biol.; 49:2219-2238.

* cited by examiner

SYSTEM AND METHOD FOR EXACT IMAGE RECONSTRUCTION FOR HELICAL CONE BEAM COMPUTED TOMOGRAPHY INCLUDING REDUNDANT DATA

This application claims the benefit of U.S. provisional application Ser. No. 60/447,428 filed Feb. 14, 2003, and U.S. provisional application Ser. No. 60/483,165 filed Jun. 27, 2003, which are incorporated herein by reference.

The following relates to the diagnostic imaging arts. It finds particular application in helical conebeam computed tomography imaging, and will be described with particular reference thereto. However, it also finds application in other types of tomographic imaging.

Exact conebeam reconstruction methods have been developed which fulfill all the requirements of the three-dimensional Radon transform. For example, an exact conebeam reconstruction method has been developed by Katsevich (see for example Katsevich et al, Proceedings SPIE Medical Imaging Conference, San Diego, Calif. (February 2003)). The Katsevich technique removes any redundant data and does not incorporate it.

In inexact three-dimensional reconstruction, redundant data is often filtered and combined. This is what is done in two-dimensional reconstructions, as in, for example, U.S. Pat. No. 4,293,912 to Walters, wherein data extending beyond opposite ends of a 180° plus fan single slice data set are weighted and combined. In the case of U.S. Pat. No. 5,446,799 of Tuy, two-dimensional redundant data is combined to improve image resolution.

The present invention contemplates an improved apparatus and method that overcomes the aforementioned limitations and others.

According to one aspect, a conebeam computed tomography imaging system is disclosed. A conebeam computed tomography scanning means is provided for acquiring oversampled conebeam projection data along a generally helical source trajectory around an examination region. An exact reconstruction means is provided, including a convolving means and an aperture-weighted backprojecting means. The convolving means is provided for performing at least one convolution of the acquired projection data. The convolving operates on projection data falling within an exact reconstruction window and on at least some redundant projection data falling outside the exact reconstruction window to produce convolved projection data. The aperture-weighted backprojecting means is provided for performing aperture-weighted backprojecting of the convolved projection data using an aperture weighting function that weightedly combines at least some convolved redundant projection data with convolved projection data falling within the exact reconstruction window to generate a reconstructed image with contributions from redundant projection data.

According to another aspect, a conebeam computed tomography imaging method is provided. Oversampled conebeam projection data is acquired along a generally helical source trajectory around an examination region. Acquired projection data falling within an exact reconstruction window and at least some acquired redundant projection data falling outside the exact reconstruction window are reconstructed into a reconstructed image with contributions from redundant projection data. The reconstructing includes convolving the acquired projection data. The convolving operates on acquired projection data falling within the exact reconstruction window and on at least some acquired redundant projection data falling outside the exact reconstruction window to produce convolved projection data. Aperture-weighted backprojecting of the convolved projection data is performed using an aperture weighting function that weightedly combines at least some convolved redundant projection data with convolved projection data falling within the exact reconstruction window to generate the reconstructed image with contributions from redundant projection data.

Incorporation of redundant data into the reconstruction is advantageous for at least two reasons. First, use of redundant data in helical reconstructions provides a continuous transition of projection data in both time and angle, significantly reducing artifacts due to data inconsistency (for example, due to anatomic motion) between ends of the reconstructed data set. Second, for a generally rectangular detector aperture, a substantial portion of the acquired projection data falls outside the pi-window or other exact reconstruction window, adversely impacting dose utilization. The substantial benefits of incorporating redundant data into the reconstruction have been demonstrated by comparison of inexact 3-pi versus pi reconstructions. Similar benefits of redundant data incorporation can be expected for exact reconstructions.

One advantage resides in improved transitions in time and angle across exact reconstruction windows.

Another advantage resides in improved dose utilization though incorporation of redundant data into exact conebeam reconstruction.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a helical conebeam computed tomography imaging system including an exact reconstruction processor that incorporates redundant data.

FIG. 2 shows an exemplary source-focused curved detector geometry.

FIG. 3 diagrammatically shows components of the hybrid convolution processor of FIG. 1.

FIG. 4 diagrammatically shows several preferred redundant data sets for incorporation into the reconstruction.

FIG. 5 compares exemplary K-planes and complementary K-planes.

Figure 8:
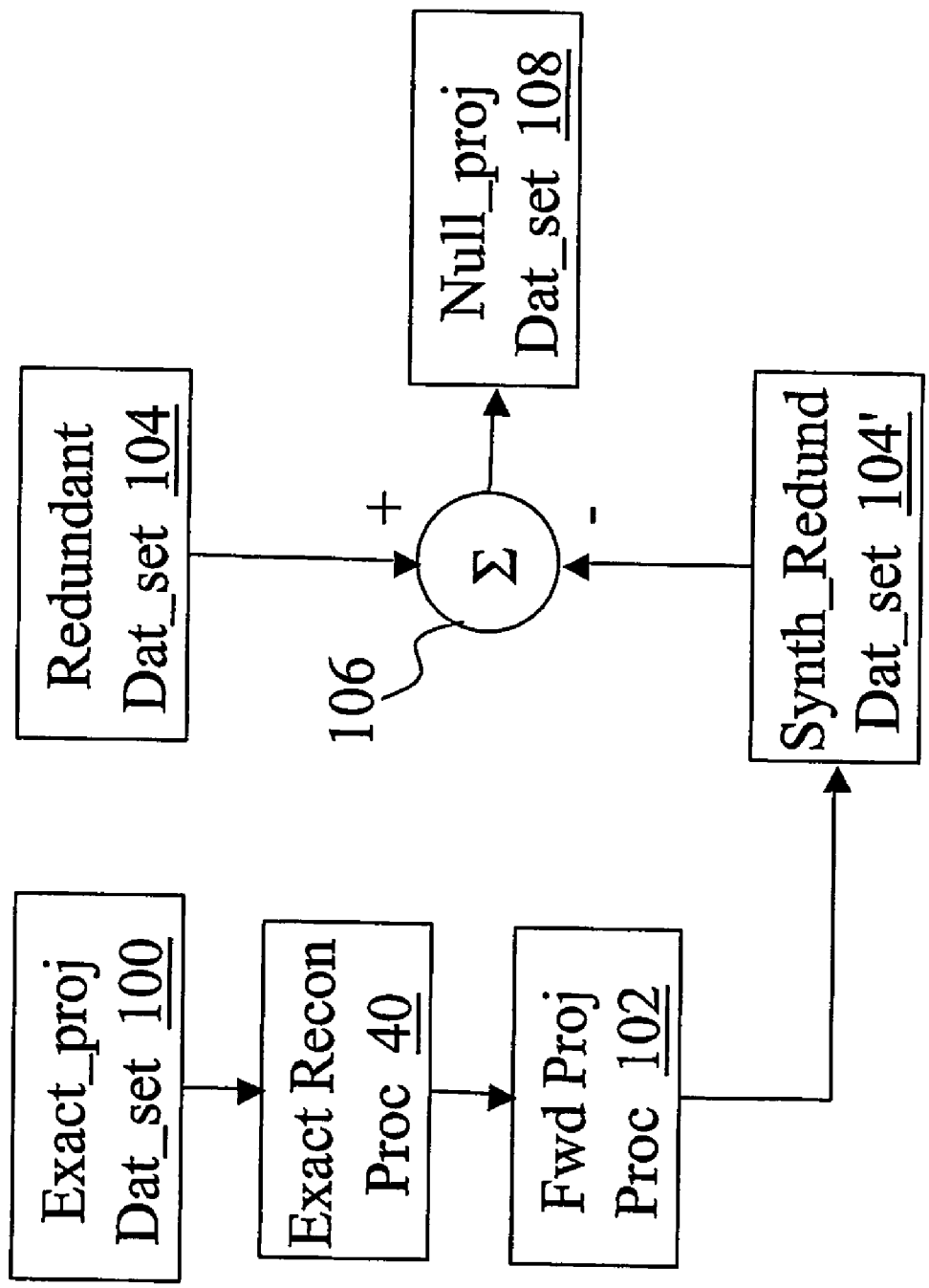

FIG. 8 diagrammatically shows an image reconstruction process that incorporates redundant data as a null data set.

Figure 1:
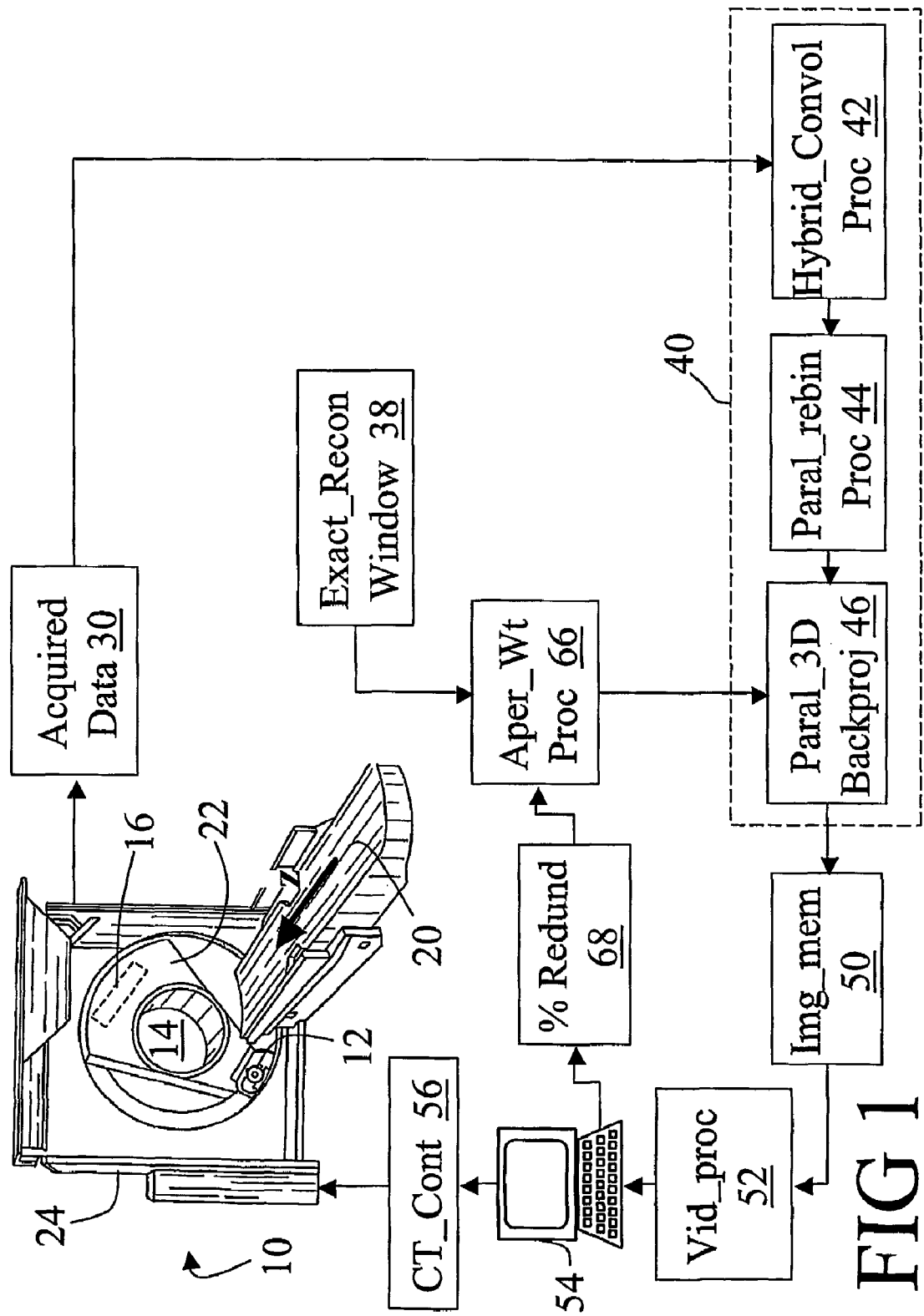
Figure 5:
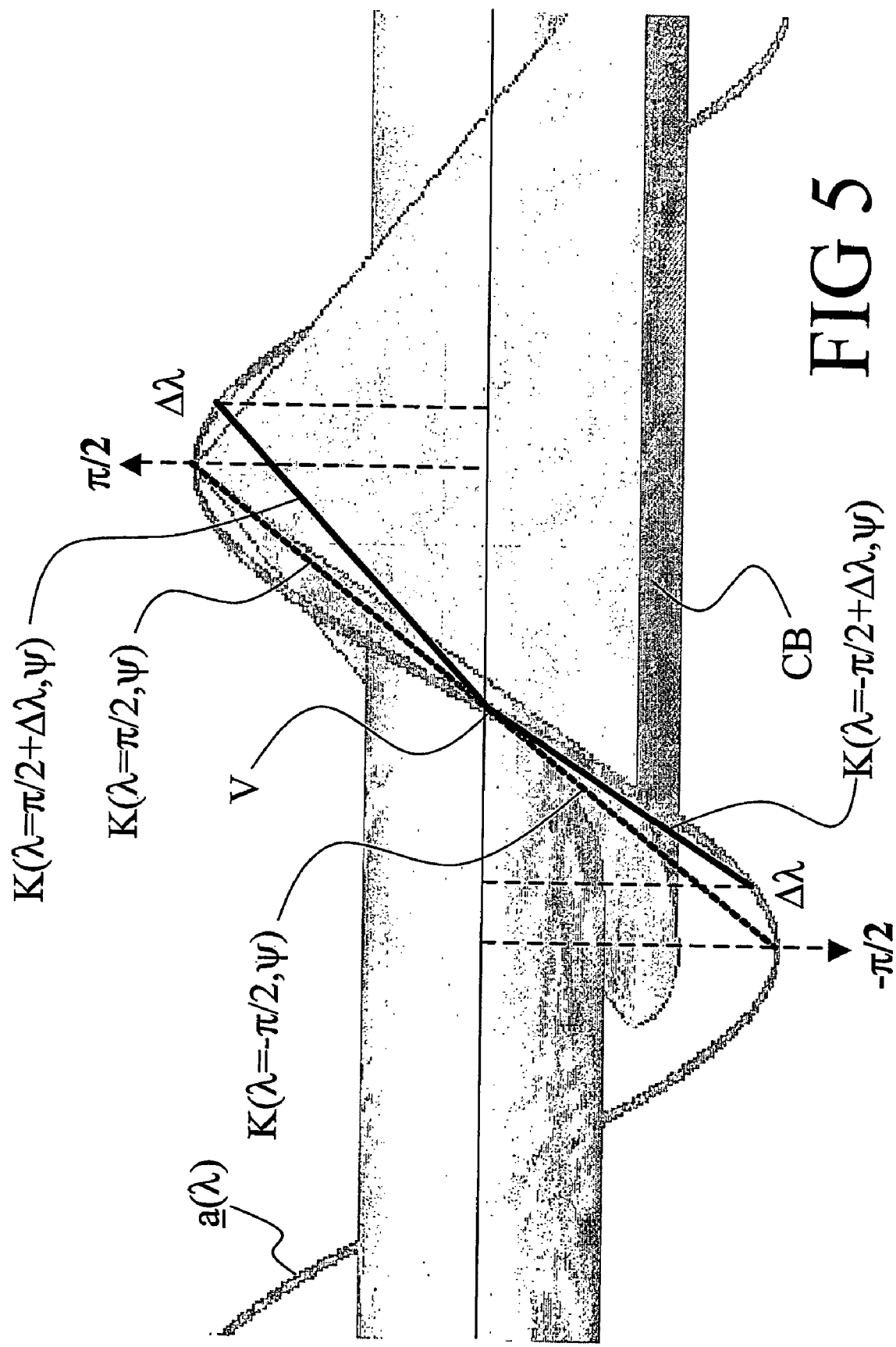
Figure 9:
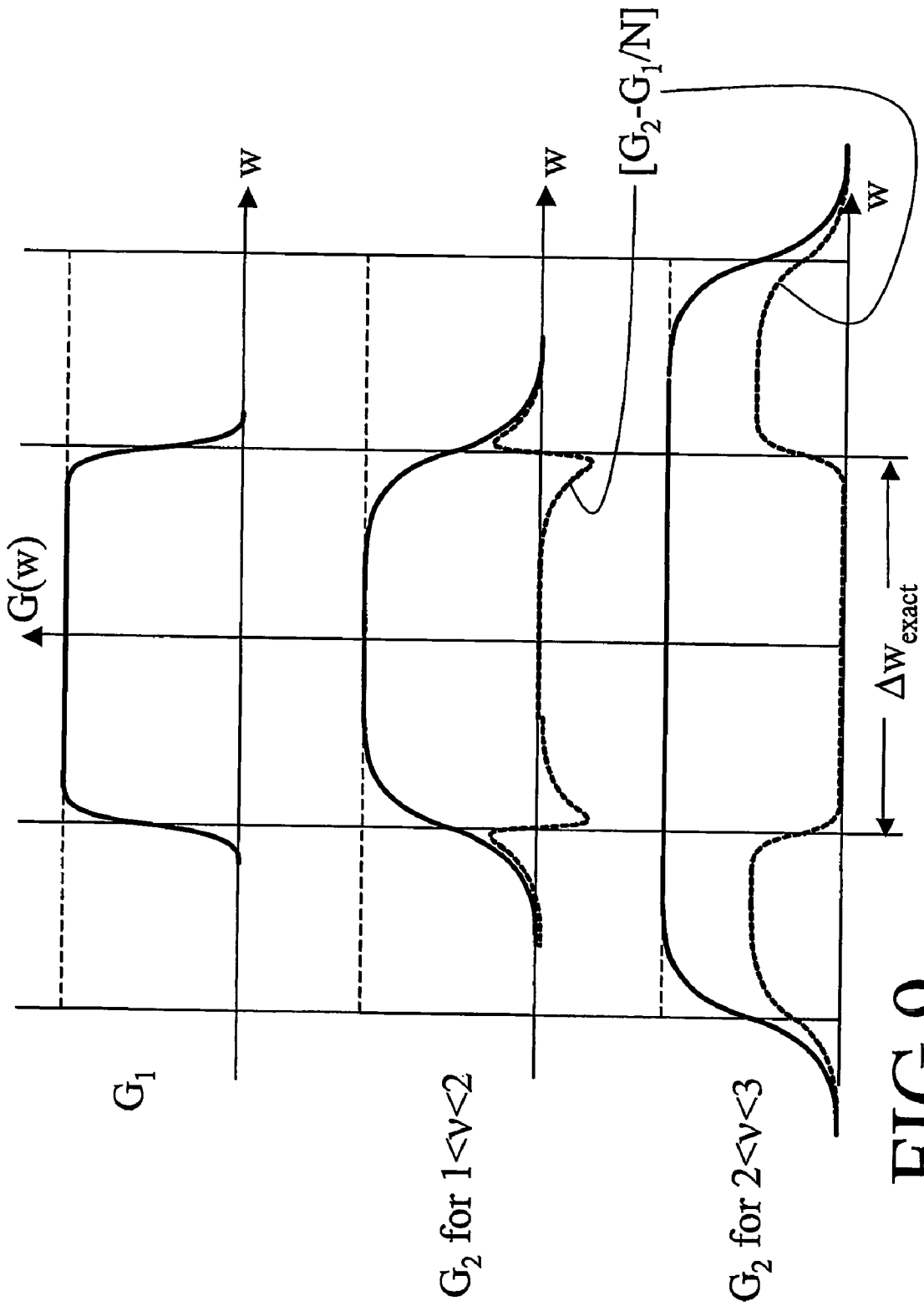

FIG. 9 shows aperture functions suitable for performing the image reconstruction process of FIG. 5 using the exact hybrid reconstruction processor of FIG. 1.

With reference to FIG. 1, a helical conebeam computed tomography imaging scanner 10 includes an x-ray source 12 that projects an x-ray conebeam into an examination region 14. After passing through the examination region, the x-ray conebeam is detected by a two-dimensional x-ray detector 16 (shown diagrammatically in phantom in FIG. 1) that includes an array of detector elements arranged to detect the x-ray conebeam after passing through the examination region 14.

To effect a helical trajectory of the x-ray source 12 about an imaging subject, the imaging subject is placed on a couch 20 or other support. The couch moves linearly along a z- or longitudinal direction as indicated. The x-ray source 12 and the x-ray detector 16 are oppositely mounted respective to the examination region 14 on a rotating gantry 22, such that rotation of the gantry 22 effects rotation of the x-ray source 12, and hence rotation of the conebeam. Rotation of the gantry 22 along with simultaneous, continuous linear motion of the couch 20 effects a helical trajectory of the x-ray source 12 and the x-ray conebeam around the imaging subject disposed on the couch 20.

The x-ray detector 16 is shown mounted on the rotating gantry 22 such that it rotates along with the x-ray source 12 to intercept the x-ray conebeam throughout the helical trajectory. However, it is also contemplated to replace the x-ray detector 16 by an x-ray detector band mounted around a stationary gantry 24.

In operation, during helical orbiting of the x-ray source 12 relative to the imaging subject, the x-ray conebeam is projected into the examination region 14 where it interacts with the imaging subject. Some portion of the x-rays are absorbed by the imaging subject to produce a generally spatially varying attenuation of the x-ray conebeam. The x-ray detector 16 measures the x-ray intensities across the conebeam to generate x-ray absorption data that is stored in an acquired projection data memory 30.

Projection data within an exact reconstruction window 38 is optionally exactly reconstructed by an exact reconstruction processor 40 that implements an exact reconstruction that fulfills the requirements of the three-dimensional Radon transform. In a preferred embodiment, the exact reconstruction processor 40 includes a hybrid convolution processor 42, a parallel rebinning processor 44, and a parallel three-dimensional backprojector 46 that cooperate to perform exact reconstruction in native scan coordinates. However, another exact conebeam reconstruction can be employed, such as the method of Katsevich (see for example Katsevich et al, Proceedings SPIE Medical Imaging Conference, San Diego, Calif. (February 2003)) which employs a voxel-based coordinate system.

The exactly reconstructed image is stored in an image memory 50 and is suitably processed by a video processor 52 to generate a three-dimensional rendering, one or more image slices, or other visual representation of the reconstructed image that is displayed on a video display of a user interface 54. Rather than a video display, the image representation can be formatted by a printer driver and printed out using a printer, transmitted over an electronic network, stored electronically, or otherwise processed. Preferably, the user interface 54 communicates with a computed tomography controller 56 to enable a radiologist or other operator to initiate imaging or otherwise control operation of the computed tomography scanner 10.

Although the exact reconstruction processor 40 can exactly reconstruct projection data within the exact reconstruction window 38 without incorporating redundant data, the resulting image representation may be degraded due to motion artifacts or noise. To reduce these effects, the reconstruction preferably incorporates redundant projection data residing outside the exact reconstruction window 38 around peripheries of aperture edges of the exact reconstruction window 38.

Preferably, the backprojector 46 is an aperture-weighted backprojector that applies aperture weighting to projection data during the backprojecting. An aperture weighting processor 66 assigns weighting values to the projection data based on a position of the projections respective to the exact reconstruction window 38. Preferably, the aperture weighting processor 66 assigns aperture weighting values selected to be substantially zero beyond a transition region at the peripheries the exact reconstruction window 38 and substantially unity inside the exact reconstruction window 38 and outside the transition region, with the transition region being a smooth and symmetric aperture weighting transition region therebetween. The size of the transition region of the aperture weighting function is selected based on a desired percentage 68 of redundant data to be incorporated into the reconstruction. The radiologist or other operator can select, via the user interface 54, to use 0% redundant data, that is, reconstruct only data within the exact reconstruction window 38, or the radiologist or other operator can select some or up to 100% of the redundant data collected by the physical detector 16.

Figure 2:
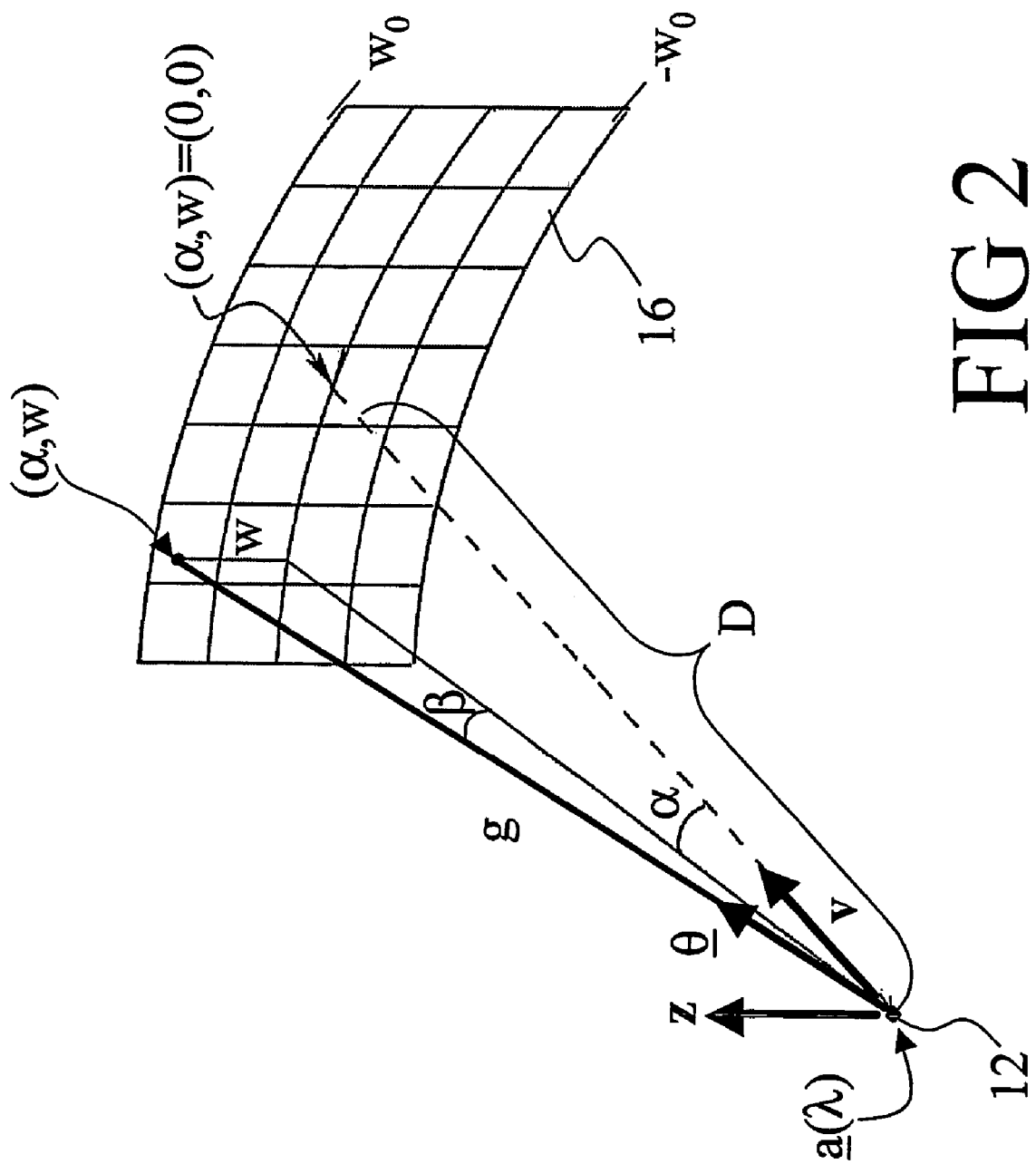

A preferred embodiment of the exact backprojection processor 40 operates in native scan coordinates. FIG. 2 diagrams native scan coordinates for a preferred source-focused curved detector geometry that comports with radiation detectors commonly used in conebeam computed tomography. A projection fan coordinate a indicates the projection angle in the fan angle direction, while a projection cone angle coordinate β indicates the projection angle in the cone angle direction. With the x-ray source 12 at a position a(λ) where λ is a helix angle of the x-ray source 12, a projection g lies along a projection direction vector θ and has coordinates g(λ, α, w) where w is a coordinate in the cone angle direction given by w=D tan(β) where D is a source-to-detector distance from the x-ray source 12 to a center of the detector 16. The coordinate w is parallel to the axial or z-direction. The lower and upper edges of the detector 16 are designated by $-w_0$ and $w_0$, respectively. The center of the curved detector 16 corresponds to projection g(λ, 0, 0), that is, α=w=0, and has a direction vector θ=v. The detector 16 is not curved along the cone angle direction, but is curved along the fan direction, that is, along the direction corresponding to the fan coordinate α. The detector curvature along the angle coordinate α is selected so that all detector elements for a given angle coordinate β are substantially equidistant from the x-ray source 12. That is, the detector curvature along the angle coordinate α is source-focused.

The preferred exact backprojection processor 40 is described with exemplary reference to the source-focused curved detector geometry diagrammed in FIG. 2. However, those skilled in the art can adapt the conebeam reconstruction processor 40 to a flat detector geometry or other detector geometry. Moreover, the backprojection processor 40 employing a hybrid convolution processor 42 operating in native scan coordinates can be replaced by another exact reconstruction processor, such as one that implements the exact reconstruction of Katsevich which operates in a voxel-based coordinate system. Still further, the redundant data incorporation methods described herein can be practiced with other substantially exact reconstruction processors. For example, the Wedge reconstruction algorithm of Tuy U.S. Pat. No. 5,446,799 has not been shown to fulfill all the requirements of the three-dimensional Radon transform; however, images reconstructed by the Wedge algorithm without redundant data can be visually indistinguishable from images reconstructed using reconstructions known to be exact.

Figure 3:
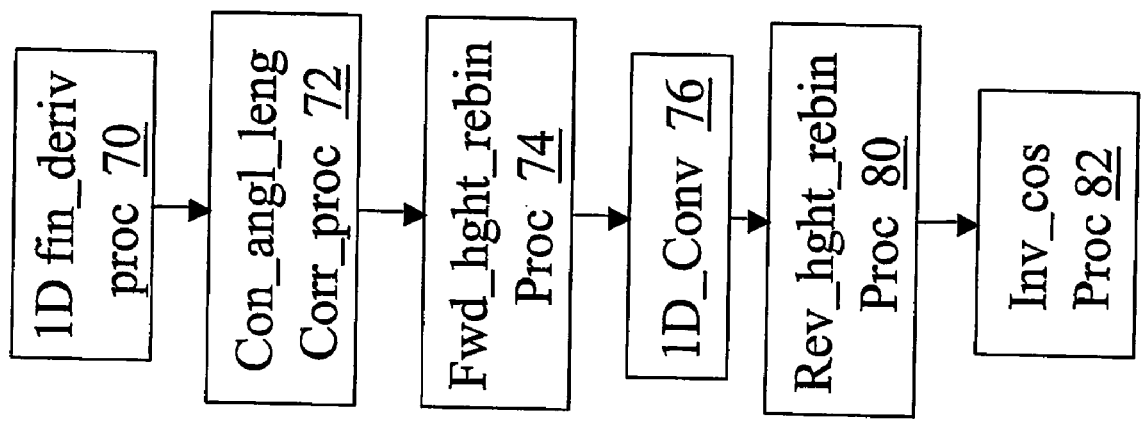

With returning reference to FIG. 1 and with further reference to FIG. 3, the hybrid convolution processor 42 performs a hybrid convolution including a differentiation convolution along the projection direction θ and a one-dimensional convolution with respect to α in a forward height-rebinned geometry.

A one-dimensional finite derivative processor 70 performs a one-dimensional derivative along the helix angle λ at constant projection direction θ according to:

$$g_{h1}(\lambda, \alpha, w) = g'(\lambda, \underline{\theta}(\lambda, \alpha, w)) = \lim_{\varepsilon \to 0} \frac{g(\lambda + \varepsilon, \underline{\theta}) - g(\lambda, \underline{\theta})}{\varepsilon}. \quad (1)$$

The derivative expressed in Equation (1) is preferably implemented as a convolution using a discrete finite difference approach, although other numerical differentiation methods known to the art can be employed. A cone angle length correction processor 72 normalizes projection lengths according to:

$$g_{h2}(\lambda, \alpha, w) = \cos(\beta) g_{h1}(\lambda, \alpha, w) = \frac{D}{\sqrt{D^2 + w^2}} g_{h1}(\lambda, \alpha, w). \quad (2)$$

The differentiated and length-normalized projection data is rebinned with respect to K-planes K(λ,ψ) by a forward height rebinning processor 74 to get constant ψ surfaces according to:

$$g_{h3}(\lambda, \alpha, \psi) = g_{h2}(\lambda, \alpha, w_K(\alpha, \psi)), \quad (3)$$

where $$w_K(\alpha, \psi) = \frac{DP}{2\pi R}\left(\psi \cos(\alpha) + \frac{\psi}{\tan(\psi)}\sin(\alpha)\right). \quad (4)$$

Equations (3) and (4) are applied over all ψ in a range [−π/2−$\alpha_m$, π/2+$\alpha_m$] where $\alpha_m$ is a fan angle defined by the size $R_{fov}$ of the field of view and the helix radius R, that is, $\alpha_m$=arcs in($R_{fov}$/R). The height-rebinned data is convolved by an FFT convolution processor 76 that performs a one-dimensional convolution with respect to α at a fixed angle ψ according to:

$$g_{h4}(\lambda, \alpha, \psi) = h_h(\sin(\alpha)) \otimes g_{h3}(\lambda, \alpha, \psi) \quad (5)$$

where ⊗ is a convolution operator and $h_h(s)=1/s$ is a Hilbert convolution kernel. A reverse height rebinning processor 80 rebins the convolved projection data according to:

$$g_{h5}(\lambda, \alpha, w) = g_{h4}(\lambda, \alpha, \psi_K(\alpha, w)) \quad (6),$$

where $ψ_K$ is the angle ψ of smallest absolute value that satisfies the equation:

$$w = \frac{DP}{2\pi R}\left(\psi \cos(\alpha) + \frac{\psi}{\tan(\psi)}\sin(\alpha)\right). \quad (7)$$

The rebinning processor 80 is optionally replaced by another rebinning processor that provides a suitable rebinning for facilitating incorporation of a selected amount of redundant data using a one-dimensional aperture weighting function. An inverse cosine weighting processor 82 weights the projection data according to:

$$g_{h6}(\lambda, \alpha, w) = g_5(\lambda, \alpha, w)/\cos(\alpha) \quad (8).$$

The parallel rebinning processor 44 rebins the convolved projection data $g_{h6}(\lambda, \alpha, w)$ into a parallel geometry according to:

$$g^F(\lambda_w, u, w) = g_6(\lambda_w + a\sin(u/R), a\sin(u/R), w) \quad (9),$$

and the filtered and rebinned projection data $g^F(\lambda_w, u, w)$ are backprojected by the aperture-weighted backprojector 46 according to:

$$f(\underline{x}) = BP_{\lambda_i;\lambda_o}\left[\frac{g^F(\lambda_w, u^*(\lambda_w, \underline{x}), w*(\lambda_w, \underline{x})) \cdot G(w*(\lambda_w, \underline{x}))}{\sum_{\lambda'_w = \lambda_w + n\pi} G(w^*(\lambda'_w, \underline{x}))}\right], \quad (10)$$

where $\lambda_w, \lambda'_w \in (\lambda_i, \lambda_o)$ which corresponds to the maximum illuminated range for the voxel at x and (u*, w*) are the interpolated projection coordinates for the projection $\lambda_w$ and voxel at x. The aperture weightings G( ) computed by the aperture weighting processor 66. Preferred aperture weightings will be described below.

The described reconstruction processor 40 has been shown by comparison with the exact voxel-based reconstruction of Katsevich to be an exact reconstruction which fulfills all the requirements of the three-dimensional Radon transform for a pi-window. Advantageously, the described reconstruction operates in native scan coordinates and incorporates the aperture-weighted parallel three-dimensional backprojector 46. A suitable aperture-weighted three-dimensional parallel backprojector 46 is described in U.S. patent application Ser. No. 10/274,816 by Heuscher et al., filed on Oct. 21, 2002.

Figure 4:
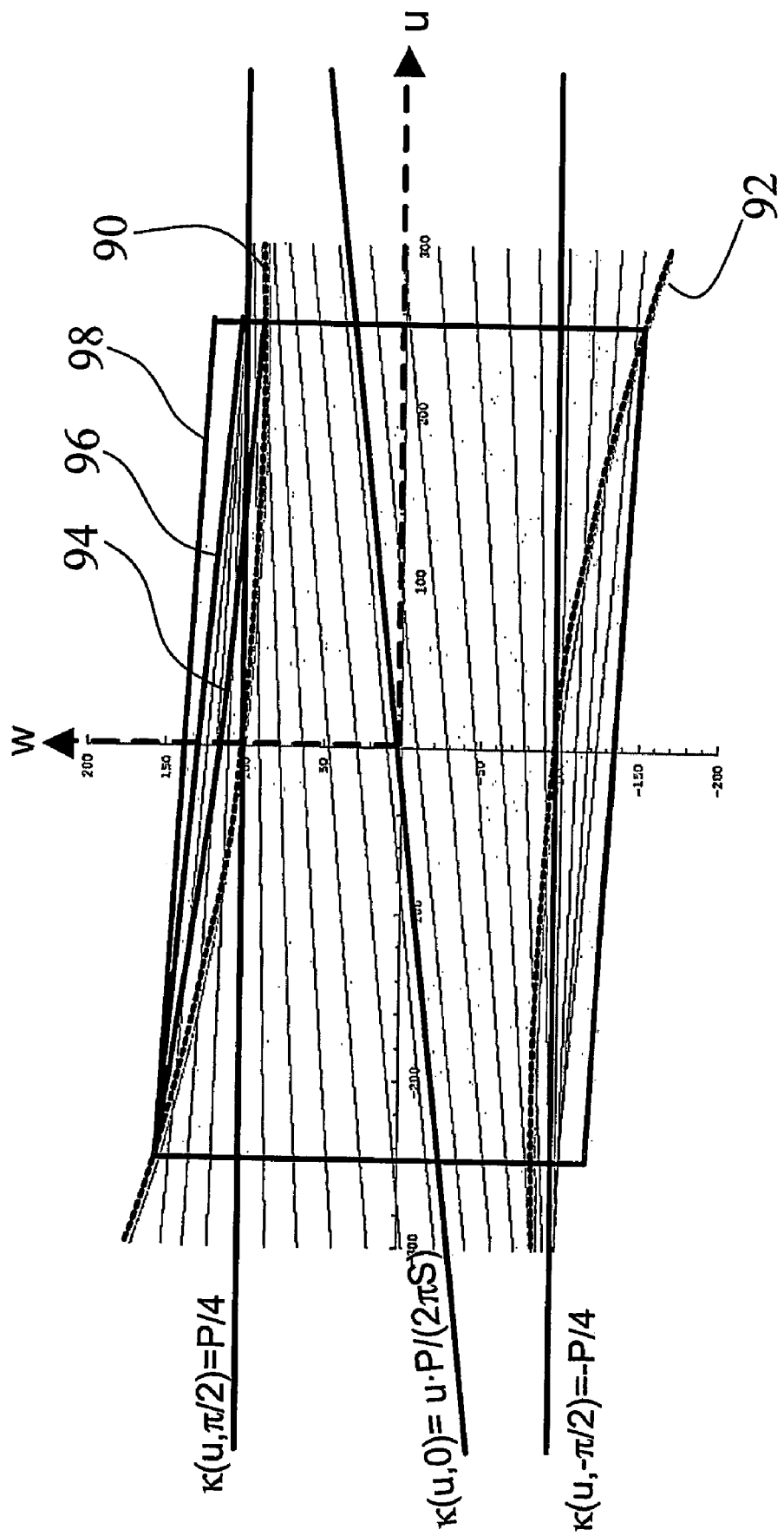

With reference to FIG. 4, several preferred redundant projection data sets are described. The coordinate u in FIG. 4 corresponds to the fan coordinate a after the parallel rebinning performed by the parallel rebinning processor 44, while the coordinate w is the aperture coordinate in the cone angle direction described previously with reference to FIG. 2. FIG. 4 shows exemplary K-planes on the detector and also indicates top and bottom curved aperture edges 90, 92 of a pi-window that is suitable for use as the exact reconstruction window 38. Each preferred redundant data set includes two symmetric parts: one above the top aperture edge 90, and the other below the bottom aperture edge 92. For convenience, only the portion of each redundant data set above the top pi-window aperture edge 90 is indicated in FIG. 4, but the described redundant data selections will be appreciated as applying to the data sets below the lower pi-window aperture edge 92.

A first preferred redundant projection data set is bounded by the aperture edge 90 and a straight line 94 in the parallel-rebinned geometry. The straight line 94 connects endpoints of the aperture edge 90 of the pi-window. This redundant projection data set is relatively small, and advantageously does not require additional rebinning operations beyond those performed by the parallel rebinning processor 44.

A second preferred redundant projection data set has bound 96 corresponding to a last projection defined by the K-planes. When using either of the redundant data sets having bounds 94, 96, the forward height rebinning processor 74 of the hybrid convolution processor 42 preferably rebins the redundant data set to K-planes in the usual way, that is, according to Equations (3) and (4).

A third preferred redundant projection data set has bound 98 corresponding to a last projection defined by modified complementary K-planes. When using the third redundant data set having bound 98, which includes more redundant data than the first and second preferred sets bounded by bounds 94, 96, the forward height rebinning processor 74 of the hybrid convolution processor 42 preferably rebins the redundant data set to modified K-planes by replacing $g_{h3}(\lambda, \alpha, \psi)$ in the convolution of Equation (5) by $g_3(\lambda, \alpha, \psi')$ where the complementary modified K-planes designated by $\psi'$ are defined as:

$$w_{K'}(\alpha,\psi'+\pi)=w_{K'}(\alpha,\psi')+\cos(\alpha)P/2 \text{ for } |\psi'|\leq\pi/2 \quad (11).$$

and $$w_{K'}(\alpha,\psi'-\pi)=w_{K'}(-\alpha,\psi')-\cos(\alpha)P/2 \text{ for } |\psi'|\leq\pi/2 \quad (12).$$

for the redundant data. Any projections that are truncated by the finite aperture of the detector 16 are preferably extrapolated according to:

$$g_3(\lambda,\alpha,\psi')=g_3(\lambda,\alpha,w_0) \text{ for all } (\alpha,\psi') \text{ s.t.} \{|w_{K'}(\alpha,\psi')|>w_0\} \quad (13).$$

where $w_0$ corresponds to the aperture edges of the x-ray detector 16 as shown in FIG. 2.

FIG. 5 illustrates complementary K-planes defined by Equations (11)–(13). A voxel on the helical axis is measured using conebeam CB which follows helical trajectory $a(\lambda)$. The K-planes $K(\lambda=-\pi/2,\psi)$ and $K(\lambda=\pi/2,\psi)$, which are shown on-edge in FIG. 5 and represented by dotted lines in FIG. 5, are fully complementary and coplanar. In contrast, the complementary K-planes $K(\lambda=-\pi/2+\Delta\lambda,\psi')$ and $K(\lambda=\pi/2+\Delta\lambda,\psi')$ indicated by the solid lines are not coplanar, leading to some inconsistency for $\Delta\lambda>0$. In other words, the complementary K-planes are bent or folded about an intersection line V containing the measured voxel. The complementary modified K-planes of Equations (11)–(13) can also be employed with the smaller first and second redundant data sets having bounds 94, 96. Those skilled in the art can select other redundant data sets; however, the described preferred redundant data sets advantageously do not require additional rebinning operations.

In employing any of the preferred redundant data sets described with reference to FIG. 4, the aperture weighting processor 66 (see FIG. 1) preferably applies a smooth normalized aperture weighting function G(w) that smooths transitions in the vicinity of aperture edges 90, 92. After processing by the hybrid convolution processor 42, the parallel rebinning processor 44 rebins the data (rebinned data shown as dotted curves in the aperture map of FIG. 6) to a wedge or other suitable rebinned geometry so that a one-dimensional normalized aperture weighting can be used to combine the redundant data with data within the exact reconstruction window. The reverse height rebinning processor 80 can be adapted to provide suitable rebinning for the selected percentage of redundant data (which may be, for example, the amount of data corresponding to a selected bound 94, 96, 98 of FIG. 4) to facilitate weighted normalization of the redundant data and complementary data using a one-dimensional aperture function G(w). A preferred form of the function G(w) satisfies the constraints of: G(w)=0 for $|w|=w_0$; G(w)=0.5 for $|w|=P/4$ (that is, at the edges 90, 92 of the exact reconstruction window); and G(w)=1 for $|w|<0.5P-w_0$. To account for data redundancy of complementary data separated by a 180° helical turn, the aperture weighting includes smoothly varying transition regions about the aperture positions $|w|=P/4$ to provide suitably weighted normalized combination of the redundant data.

Figure 6:
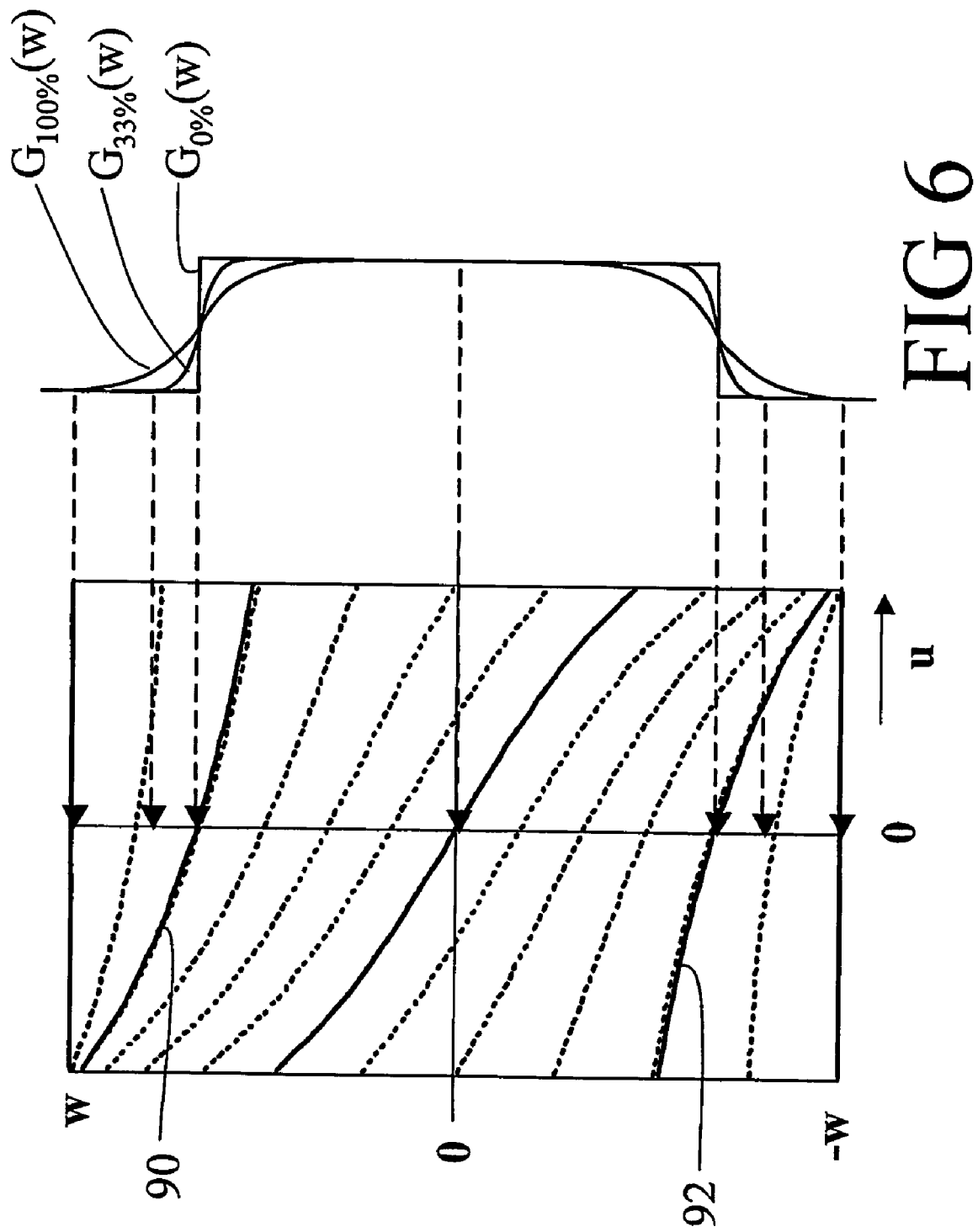
FIG. 6 shows selection of suitable aperture weighting functions G(w) for including 100%, 33%, and 0% of redundant data into the reconstruction.

FIG. 6 shows exemplary weighting functions $G_{100\%}(w)$, $G_{33\%}(w)$, and $G_{0\%}(w)$ which are appropriate for inclusion of 100% of redundant data, 33% of redundant data, and 0% of redundant data, respectively, for a voxel on the helix axis. For 0% redundant data, $G_{0\%}(w)$ is a rectangular aperture weighting that retains data within the exact reconstruction window while discarding the redundant data outside the exact reconstruction window. In contrast, aperture weighting $G_{33\%}(w)$ includes a limited transition region that effects weighted combination of some redundant data from outside the exact reconstruction window. The reduced aperture weight in the transition region outside the exact reconstruction window versus complementary projection data residing in the transition region inside the exact reconstruction provides greater weight to the data inside the exact reconstruction window, but still allows some contribution from the redundant data outside the reconstruction window but near the aperture edges 90, 92. Aperture weighting $G_{100\%}(w)$ provides for incorporation of more redundant data versus $G_{33\%}(w)$ by further increasing the width of the transition regions.

Figure 7:
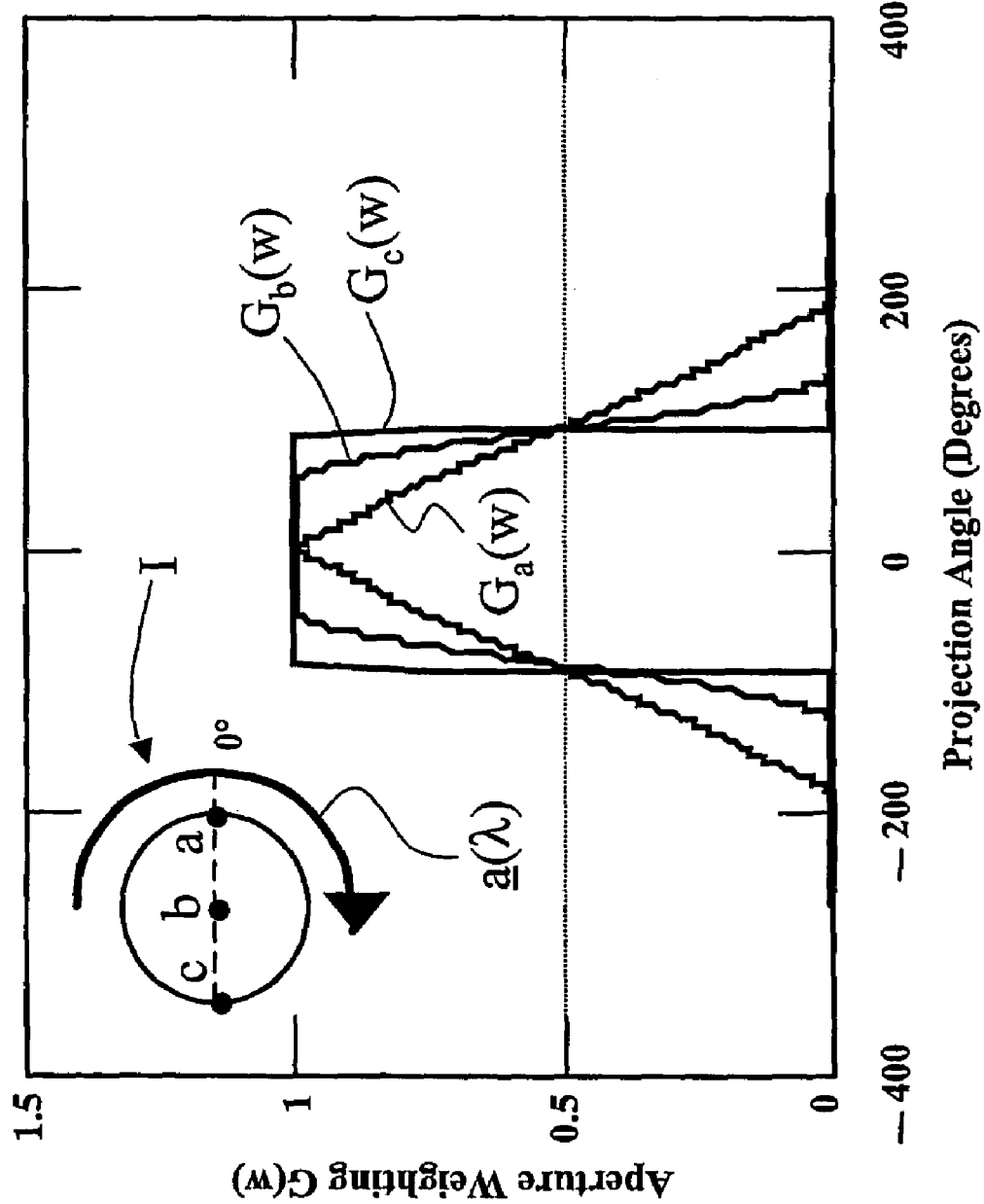
FIG. 7 shows selection of suitable aperture weighting functions G(w) for voxels at different positions relative to the helical axis.

FIG. 7 shows how the aperture weighting varies depending upon the position of the voxel relative to the helical axis. Inset I of FIG. 7 diagrammatically shows the field of view (represented by a circle), a portion of the helical trajectory $a(\lambda)$ employed in data acquisition for the voxels of interest, and three voxels labeled a, b, c positioned closest to the helical trajectory portion, on the helical axis, and furthest from the helical trajectory portion, respectively. The corresponding aperture weighting functions $G_a(w)$, $G_b(w)$, $G_c(w)$ are shown in the graph of FIG. 7.

For the voxel c, limited redundant data is acquired due to the distance of voxel c from the x-ray source during data acquisition. The corresponding $G_c(w)$ has small transition regions and is close to corresponding to the exact reconstruction window. For the voxel a which is close to the helical trajectory portion, substantial redundant data is acquired and so $G_a(w)$ has very broad transition regions to incorporate the substantial redundant data. For voxel b which is intermediate between voxel a and voxel c, an intermediate aperture function $G_b(w)$ is appropriate. It will be observed that all the aperture weighting functions $G_a(w)$, $G_b(w)$, $G_c(w)$ are normalized such that G(w)=0.5 at the edges 90, 92 of the exact reconstruction window, G(w) rises smoothly toward unity near the center of the exact reconstruction window, and decreases smoothly toward zero outside the exact reconstruction window.

With reference to FIG. 8, another suitable approach for incorporating redundant data into a reconstruction employing the exact reconstruction processor 40 is described. The approach of FIG. 8 takes advantage of the capability of the exact reconstruction processor 40 (shown as a single block in FIG. 8) to perform an exact reconstruction of an exact projection data set 100 lying within the exact reconstruction window 38. The exactly reconstructed image is reprojected by a forward projection operator 102 over at least a range corresponding to an acquired redundant projection data set 104. This reprojection produces a synthetic redundant data set 104' over a range corresponding to the acquired redundant projection data set 104.

Because the exact reconstruction processor 40 performs exact reconstruction of the exact projection data set, it follows that the synthetic projection data is identical to the exact projection data set 100 within the exact reconstruction window 38. Moreover, in the absence of noise, motion artifacts, or other inconsistencies, the synthetic redundant projection data set 104' in the range of the redundant data set 104 is identical to the redundant projection data set 104.

Thus, a combining block 106 suitably subtractively combines the synthetic redundant projection data set 104' with the acquired redundant projection data set 104 to produce a null projection data set 108. Combining the exact projection data set 100 and the null projection data set 108 in the exact reconstruction 40 thus provides improved continuity of projection data across time and angle transitions, which in turn reduces artifacts due to data inconsistency and can reduce noise by averaging over the additional redundant data embodied by the null data set 108.

With returning reference to FIG. 1 and further reference to FIG. 9, a preferred approach for performing a v-pi reconstruction with a null projection data set is as follows. The hybrid convolution processor 42 convolves the acquired projection data and the rebinning processor 44 rebins the projection data to produce an exact hybrid convolved data set $P_1$ corresponding to the projections $g^F(\lambda_w, u, w)$ of Equation (9). The aperture weighting processor 66 and backprojector 46 perform aperture-weighted backprojection using a smooth weighting function $G_1(w)$ shown in FIG. 9 having a passband $\Delta w_{exact}$ substantially corresponding to the aperture width of the exact reconstruction window 38. The exact reconstructed image is re-projected by the forward projection processor 102 to define a synthetic projection data set $P_2$ that spans at least the exact reconstruction window 38 and the range of the redundant projection data set. A projection data set $P_1'$ is constructed by filtering the data set $P_1$ to make sure projections have the same spatial response as the synthetic projection data set $P_2$. The projection data set ($P_1'-P_2$) is the null projection data set 108. To account for the original transition region of the aperture weighting function $G_1(w)$, the final reconstructed image is preferably generated according to:

$$I_{final} = AWBP(G_1, P_1) + [AWBP(G_2, (P_1'-P_2)) - AWBP(G_1, (P_1'-P_2))]/N \quad (14),$$

where: $G_2(w)$ is a second aperture weighting function having an extended passband that is larger than the passband $\Delta w_{exact}$ and encompasses the exact reconstruction window 38 and the range of the redundant projection data set; AWBP( ) represents the aperture-weighted backprojection performed AWBP( ) according to Equation (10) by the backprojector 46; N is the largest integer less than v; and $I_{final}$ is the final reconstructed image with contributions from the exact projection data set and from the null projection data set.

FIG. 9 shows two exemplary $G_2(w)$ weighting functions: one for a range 1<v<2; and one for a range 2<v<3. The term in brackets in Equation (14) is an image correction corresponding to the null data set weighted by [$G_2-G_1/N$] after aperture-weighted normalization. The [$G_2-G_1/N$] weighting is indicated in FIG. 9 by dotted lines.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A conebeam computed tomography imaging system including:
   a conebeam computed tomography scanning means (10) for acquiring oversampled conebeam projection data along a generally helical source trajectory around an examination region (14); and
   an exact reconstruction means (40) including:
      a convolving means (42) for performing at least one convolution of the acquired projection data, the convolving operating on projection data falling within an exact reconstruction window (38) and on at least some redundant projection data falling outside the exact reconstruction window (38) to produce convolved projection data, and
      an aperture-weighted backprojecting means (46, 66) for performing aperture-weighted backprojecting of the convolved projection data using an aperture weighting function that weightedly combines at least some convolved redundant projection data with convolved projection data falling within the exact reconstruction window (38) to generate a reconstructed image with contributions from redundant projection data.

2. The imaging system as set forth in claim 1, wherein the convolving means (42) includes:
   a height rebinning means (74) for height-rebinning projections along K-planes.

3. The imaging system as set forth in claim 2, wherein the height rebinning means (74) rebins redundant projection data falling outside the exact reconstruction window (38) to modified K-planes that are folded about a pi-line respective to K-planes corresponding to complementary projection data falling within the exact reconstruction window (38).

4. The imaging system as set forth in claim 2, wherein the height rebinning means (74) rebins redundant projection data falling outside the exact reconstruction window (38) to K-planes that are complementary to K-planes corresponding to projection data falling within the exact reconstruction window (38).

5. The imaging system as set forth in claim 2, wherein the exact reconstruction window (38) is a pi-window, and the aperture-weighted backprojecting means (46, 66) employs an aperture weighting function that combines redundant projection data lying between an edge (90, 92) of the pi-window and a line (94) connecting endpoints of the edge of the pi-window with complementary projection data lying within the pi-window.

6. The imaging system as set forth in claim 1, wherein the aperture-weighted backprojecting means (46, 66) employs a smoothly varying aperture weighting function G(w) that satisfies the criteria:
   $G(w)=0$ at $|w|=w_0$,
   $G(w)=0.5$ at $|w|=P/4$, and
   $G(w)=1$ at $|w| \leq (0.5P-w_0)$,
   where w is a coordinate in the cone angle direction, $w_0$ corresponds to aperture edges of a radiation detector (16) of the conebeam computed tomography scanning means (10), and P corresponds to a helical pitch of the generally helical trajectory.

7. The imaging system as set forth in claim 1, wherein the aperture-weighted backprojecting means (46, 66) employs a smoothly varying aperture weighting function whose value is selected to be substantially zero outside the exact reconstruction window (38) and substantially unity inside the exact reconstruction window (38) with a smooth aperture weighting transition region therebetween.

8. The imaging system as set forth in claim 1, further including:
   a means (102) for forward projecting an exact reconstructed image formed by applying the exact reconstruction means (40) to an exact projection data set (100) falling within the exact reconstruction window (38) to generate simulated projection data corresponding to the convolved redundant projection data that is to be weightedly combined with convolved projection data falling within the exact reconstruction window (38); and a means (106) for combining the simulated projection data and convolved projection data to generate a null projection data set (108).

9. The imaging system as set forth in claim 8, wherein:
in the applying of the exact reconstruction means (40) to the exact projection data set (100), the aperture weighted backprojecting means (46, 66) applies a first aperture weighting function ($G_1$) to the exact projection data set (100) to produce a nonredundant exact reconstructed image, the first aperture weighting function ($G_1$) having a first aperture passband ($\Delta W_{exact}$) substantially corresponding to the exact reconstruction window (38).

10. The imaging system as set forth in claim 9, wherein:
the reconstructed image with contributions from redundant projection data is generated by the aperture-weighted backprojecting means (46, 66) by:
backprojecting the null projection data set (108) weighted by the first aperture weighting function ($G_1$) to generate a first null reconstructed image,
backprojecting the null projection data set (108) weighted by an extended aperture weighting function ($G_2$) having an extended aperture passband substantially encompassing both the exact reconstruction window (38) and at least some redundant data set to generate a second null reconstructed image, and
combining the nonredundant exact reconstructed image, the first null reconstructed image, and the second null reconstructed image.

11. The imaging system as set forth in claim 8, wherein the exact reconstruction means (40) reconstructs the null projection data set (108) into at least one null reconstructed image, the reconstructed image with contributions from redundant projection data being generated by combining an image reconstructed by the reconstructing means (40) from the convolved projection data and the at least one null reconstructed image.

12. The imaging system as set forth in claim 1, wherein the exact reconstruction means (40) performs a reconstruction that satisfies the requirements of the three-dimensional Radon transform for projection data falling within the exact reconstruction window (38).

13. A conebeam computed tomography imaging method including:
acquiring oversampled conebeam projection data along a generally helical source trajectory around an examination region (14); and
reconstructing acquired projection data falling within an exact reconstruction window (38) and at least some acquired redundant projection data falling outside the exact reconstruction window (38) into a reconstructed image with contributions from redundant projection data, the reconstructing including:
convolving the acquired projection data, the convolving operating on acquired projection data falling within the exact reconstruction window (38) and on at least some acquired redundant projection data falling outside the exact reconstruction window (38) to produce convolved projection data, and
performing aperture-weighted backprojecting of the convolved projection data using an aperture weighting function that weightedly combines at least some convolved redundant projection data with convolved projection data falling within the exact reconstruction window (38) to generate the reconstructed image with contributions from redundant projection data.

14. The imaging method as set forth in claim 13, wherein the convolving includes:
rebinning projection data to K-planes; and
performing at least two convolution operations, at least one of which is performed after the rebinning to K-planes.

15. The imaging method as set forth in claim 14, wherein the rebinning of projection data along K-planes includes:
rebinning projection data falling within the exact reconstruction window (38) to first K-planes; and
rebinning redundant projection data falling outside the exact reconstruction window (38) to modified K-planes that are complementary to at least some of the first K-planes.

16. The imaging method as set forth in claim 13, wherein the exact reconstruction window (38) is a pi-window, and the performing of aperture-weighted backprojecting includes:
weightedly combining convolved projection data lying outside the pi-window along a periphery of edges (90, 92) of the pi-window with convolved projection data falling within the exact reconstruction window (38).

17. The imaging method as set forth in claim 13, wherein the aperture-weighting function includes:
substantially zero weighting values outside the exact reconstruction window (38);
substantially unity weighting values inside the exact reconstruction window (38); and
weighting values smoothly varying between zero and unity in a transition region disposed at a periphery of the exact reconstruction window (38).

18. The imaging method as set forth in claim 13, wherein the aperture-weighting function is a one-dimensional aperture weighting function.

19. The imaging method as set forth in claim 13, wherein the performing aperture-weighted backprojecting includes:
aperture-weighting the rebinned projection data using a normalized one-dimensional smooth aperture weighting function that normalizes contributions of complementary projections, the aperture weighting function having:
smoothly varying normalization weighting values for projections in a transition region substantially centered on edges (90, 92) of the exact reconstruction window (38);
a substantially unity weighting value inside the exact reconstruction window (38) and outside the transition region; and
a substantially zero weighting value outside the exact reconstruction window (38) and outside the transition region.

20. The imaging method as set forth in claim 13, further including:
reconstructing an exact portion of projection data falling within the exact reconstruction window (38) into a nonredundant exact reconstructed image using a reconstruction that satisfies the requirements of the three-dimensional Radon transform;
forward projecting the nonredundant exact reconstructed image to generate a simulated projection data set extending outside the exact reconstruction window (38); and combining the simulated projection data set and convolved projection data including at least some convolved redundant projection data to form a null projection data set (108).

21. The imaging method as set forth in claim 20, wherein the performing of aperture-weighted backprojecting of the convolved projection data using an aperture weighting function that weightedly combines at least some convolved redundant projection data with convolved projection data falling within the exact reconstruction window (38) includes:

reconstructing the null projection data set (108) into at least one null reconstructed image; and combining the nonredundant exact reconstructed image and the at least one null reconstructed image (108).

22. The imaging method as set forth in claim 13, wherein the performing of aperture-weighted backprojecting of the convolved projection data using an aperture weighting function that weightedly combines at least some convolved redundant projection data with convolved projection data falling within the exact reconstruction window (38) includes:

reconstructing the acquired projection data weighted by a first aperture function substantially corresponding to the exact reconstruction window (38) into a nonredundant exact reconstructed image;

forward projecting the nonredundant exact reconstructed image to generate a simulated projection data set extending outside of the exact reconstruction window (38); and combining the simulated projection data set and the acquired projection data to form a null projection data set (108).

23. The imaging method as set forth in claim 22, wherein the performing of aperture-weighted backprojecting of the convolved projection data using an aperture weighting function that weightedly combines at least some convolved redundant projection data with convolved projection data falling within the exact reconstruction window (38) further includes:

reconstructing the null projection data set (108) weighted by an extended aperture function that spans a larger aperture range than the first aperture function into a first null reconstructed image;

reconstructing the null projection data set (108) weighted by the first aperture function into a second null reconstructed image; and combining the nonredundant exact reconstructed image, the first null reconstructed image, and the second null reconstructed image to form the reconstructed image with contributions from redundant projection data.

24. The imaging method as set forth in claim 23, wherein the combining of the nonredundant exact reconstructed image, the first null reconstructed image, and the second null reconstructed image includes:

subtractively combining the second null reconstructed image from the first null reconstructed image to generate an image correction; and correcting the nonredundant exact reconstructed image by the image correction.

\* \* \* \* \*